US00PP36656P2

(12) United States Plant Patent
Carrella

(10) Patent No.: US PP36,656 P2
(45) Date of Patent: May 6, 2025

(54) ***CALIBRACHOA* PLANT NAMED 'KLECA22913'**

(50) Latin Name: ***Calibrachoa* sp.**
Varietal Denomination: KLECA22913

(71) Applicant: KLEMM + SOHN GMBH & CO. KG, Stuttgart (DE)

(72) Inventor: Angelo Carrella, Palma Campania (IT)

(73) Assignee: KLEMM + SOHN GMBH & CO. KG, Stuttgart (DE)

( * ) Notice: Subject to any disclaimer, the term of this patent is extended or adjusted under 35 U.S.C. 154(b) by 0 days.

(21) Appl. No.: 18/762,984

(22) Filed: Jul. 3, 2024

(51) Int. Cl.
*A01H 5/02* (2018.01)
*A01H 6/82* (2018.01)

(52) U.S. Cl.
USPC ..... Plt./413
CPC ..... *A01H 6/821* (2018.05)

(58) Field of Classification Search
USPC ..... Plt./413
CPC ..... A01H 5/02
See application file for complete search history.

(56) References Cited

PUBLICATIONS https://selecta-one.com/katalog/index.php?catalog=Spring_Trixi_2023_24_NE; Oct. 8, 2024; 83 pages.*

* cited by examiner

*Primary Examiner* — Kent L Bell
(74) *Attorney, Agent, or Firm* — Weatherly IP Solutions, LLC; James M. Weatherly

(57) ABSTRACT

A new *Calibrachoa* plant particularly distinguished by having a pink flowers with a dark purple center; and a semi-mounding plant habit, is disclosed.

1 Drawing Sheet

Genus and species: *Calibrachoa* sp.
Variety denomination: 'KLECA22913'.

BACKGROUND OF THE NEW PLANT

The present invention comprises a new and distinct variety of *Calibrachoa*, botanically known as *Calibrachoa* sp., and hereinafter referred to by the variety name 'KLECA22913'. 'KLECA22913' originated from a controlled-cross between the proprietary female *Calibrachoa* variety 'CA-2018-2924' (unpatented) and the male *Calibrachoa* variety 'CA-2018-2242' (unpatented).

In August 2018, two *Calibrachoa* parental lines, the female variety 'CA-2018-2924' and the male variety 'CA-2018-2242' were crossed via a controlled-cross in Stuttgart, Germany and seeds were obtained. The seeds were sown and plants were grown for evaluation. A plant line was selected in May 2019 and subsequently named 'KLECA22913'. In May 2019, 'KLECA22913' was first vegetatively propagated by cuttings in Stuttgart, Germany. 'KLECA22913' was found to reproduce true to type in successive generations of asexual propagation via cuttings.

SUMMARY

The following are the most outstanding and distinguishing characteristics of this new variety when grown under normal horticultural practices in Stuttgart, Germany.

1. Pink flowers with a dark purple center; and
2. Semi-mounding plant habit.

DESCRIPTION OF THE PHOTOGRAPH

This new *Calibrachoa* plant is illustrated by the accompanying photograph which shows a close-up of the whole plant. The photograph is of a 12-week-old-plant grown in a greenhouse in Stuttgart, Germany in February 2023. The colors shown are as true as can be reasonably obtained by conventional photographic procedures.

DESCRIPTION OF THE NEW VARIETY

The following detailed descriptions set forth the distinctive characteristics of 'KLECA22913'. The data which define these characteristics were collected from asexual reproductions carried out in Stuttgart, Germany. Data was collected on 14-week old plants after transplant in Latina, Italy. Color references are to The R.H.S. Colour Chart of The Royal Horticultural Society of London (R.H.S.), 5$^{th}$ edition (2007).

Classification:
*Family.*—Solanaceae.
*Species.*—*Calibrachoa* sp.
*Common name.*—*Calibrachoa.*

Parentage:
*Female.*—CA-2018-2924.
*Male.*—CA-2018-2242.

Plant description:
*Life cycle.*—Annual.
*Form.*—Short-lived subshrub.
*Habit.*—Semi-mounding.
*Height (from soil line to top of foliage).*—8.1 cm.
*Spread.*—31.2 cm.

Propagation:
*Type cuttings.*—Tip cuttings.
*Time to produce a rooted cutting.*—3 weeks.

Stems:
*Stem color.*—RHS 145B.

*Pubescence color*.—RHS 155A.
*Stem diameter*.—0.1 cm.
*Stem length*.—From soil line to first node: 1.1 cm. Total length: 9.2 cm.
*Internode length*.—1.2 cm.

Leaves:
*Arrangement*.—Alternate.
*Shape*.—Cuneate.
*Apex*.—Obtuse.
*Base*.—Acute.
*Margin*.—Ciliate.
*Surface pubescence*.—Present.
*Pubescence color*.—RHS 155A.
*Venation color*.—Upper surface: RHS 138A. Lower surface: RHS 138B.
*Venation pattern*.—Very weak.
*Length*.—2.7 cm (mature leaves).
*Width*.—0.9 cm (mature leaves).
*Color*.—Upper surface: RHS 138A. Lower surface: RHS 138B.
*Fragrance*.—Absent.

Petioles:
*Length*.—2.0 cm to 9.0 cm.
*Diameter*.—0.2 cm.
*Texture*.—Pubescent.
*Color*.—RHS 137B.

Flowers:
*Flowering habit*.—Single flower.
*Flower type*.—Single.
*Flowering requirements*.—A minimum amount of sun light is required.
*Duration of flowers*.—7 days.
*Corolla texture*.—Smooth (both upper and lower surfaces).
*Shape*.—Funnel form.
*Fragrance*.—Absent.
*Typical and observed number of flowers per plant per season*.—More than 60 flowers per plant per season cultivated indoors in pot size 14 one week after starting to flower.

Flower buds:
*Surface*.—Pubescent.
*Length*.—1.6 cm.
*Diameter*.—0.3 cm.
*Shape*.—Irregular to oblong.
*Color*.—RHS 75D (top buds) 145C (base buds).
*Typical and observed number of flower buds per plant per season*.—More than 60 flower buds per plant per season cultivated indoors in pot size 14.

Peduncle:
*Length*.—1.4 cm.
*Diameter*.—Less than 0.1 cm.
*Color*.—RHS 144B.
*Texture*.—Pubescent.
*Anthocyanin color*.—Absent.

Flower description:
*Flower depth*.—2.3 cm.
*Flower tube length*.—1.5 cm.
*Flower tube diameter*.—0.8 cm.
*Flower diameter*.—3.4 cm.
*Throat diameter*.—0.9 cm.
*Pedicel color*.—RHS 144B.

Sepals:
*Typical and observed number of sepals per flower*.—5 sepals for each calyx.
*Shape*.—Ovate.
*Apex*.—Obtuse.
*Margin*.—Ciliate.
*Length*.—1.1 cm.
*Diameter*.—0.3 cm.
*Sepal color*.—Upper surface: RHS 137B. Lower surface: RHS 138A.
*Sepal texture*.—Upper surface: Pubescent. Lower surface: Pubescent.

Petals:
*Typical number*.—Five.
*Shape*.—Obcordate.
*Length*.—1.3 cm.
*Apex*.—Obtuse.
*Margin*.—Entire.
*Base*.—Fused into a tube.
*Pubescence*.—Absent.
*Lobe length*.—1.3 cm.
*Lobe width*.—1.2 cm.
*Venation color*.—Very weak.
*Color*.—Lobe color: Upper surface: RHS N74C main color, center RHS N74A. Lower surface: RHS 75C. Corolla tube color: Inner: RHS 2C. Outer: RHS 1C.
*Fragrance*.—Absent.

Reproductive organs:
*Stamen number*.—5.
*Anther color*.—RHS 13B.
*Anther length*.—0.1 cm.
*Filament color*.—RHS 1C.
*Filament length*.—0.8 cm.
*Pollen color*.—RHS 12A.
*Pollen amount*.—Moderate.
*Ovary*.—Placenta arrangement.—Ovate. Pistil number.—1.Pistil length.—0.6 cm. Stigma color.—RHS 145B. Stigma shape.—Round. Style length.—0.5 cm. Style color.—RHS 145B.

Fruit/seed set: None observed.

Disease/insect resistance: No pests and disease were observed.

COMPARISON WITH PARENTAL LINES AND KNOWN VARIETY

'KLECA22913' is distinguished from its parents as described in Table 1 and Table 2:

TABLE 1

| Comparison with Female Parent | | |
|---|---|---|
| Trait | Variety 'KLECA22913' | Female parent 'CA-2018-2924' |
| Earliness | 37 days from potting to flowering | 43 days from potting to flowering |

TABLE 2

| Comparison with Male Parent | | |
|---|---|---|
| Trait | Variety 'KLECA22913' | Male Parent 'CA-2018-2242' |
| Main flower color | Pink | Orange |

'KLECA22913' is most similar to the *Calibrachoa* plant named 'KLECA23899' (U.S. application Ser. No. 18/763,058). Differences between the two varieties are described in Table 3:

TABLE 3

| Comparison with Similar Variety | | |
|---|---|---|
| Trait | Variety 'KLECA22913' | Commercial line 'KLECA23899' |
| Flower petal color pattern | Pink with dark purple center | Pink without dark center |

I claim:

1. A new and distinct cultivar of *Calibrachoa* Plant Named 'KLECA22913' as shown and described herein.

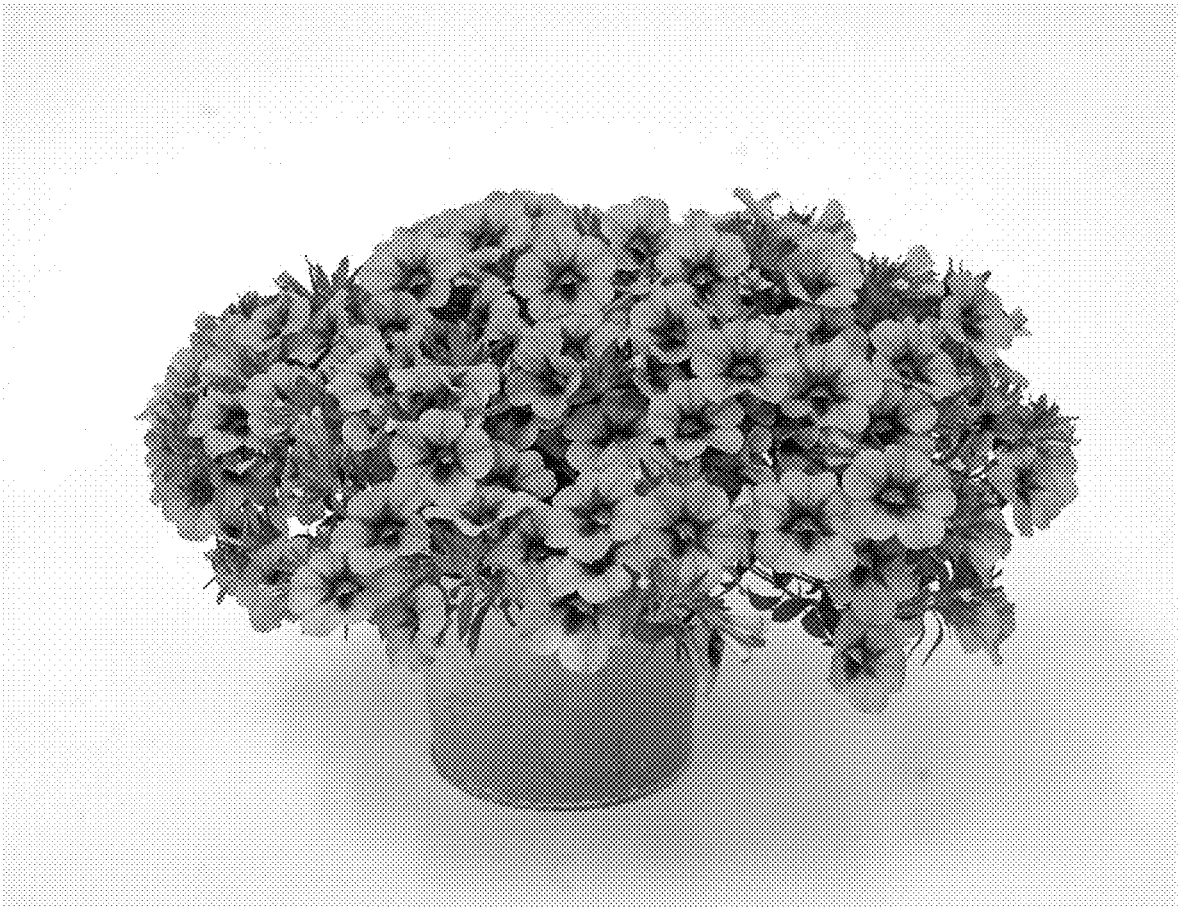

* * * * *